US009669001B2

(12) United States Patent
Bowler et al.

(10) Patent No.: US 9,669,001 B2
(45) Date of Patent: *Jun. 6, 2017

(54) ANTIMICROBIAL COMPOSITION

(75) Inventors: Phillip Godfrey Bowler, Flintshire (GB); Daniel Gary Metcalf, Flintshire (GB); David Parsons, West Kirby (GB)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/124,472

(22) PCT Filed: Dec. 18, 2009

(86) PCT No.: PCT/GB2009/002912
§ 371 (c)(1),
(2), (4) Date: Sep. 13, 2011

(87) PCT Pub. No.: WO2010/070292
PCT Pub. Date: Jun. 24, 2010

(65) Prior Publication Data
US 2011/0319808 A1 Dec. 29, 2011

(30) Foreign Application Priority Data
Dec. 20, 2008 (GB) .................................. 0823265.4

(51) Int. Cl.
*C12Q 1/04* (2006.01)
*A61K 31/325* (2006.01)
*A61K 31/352* (2006.01)
*A61N 5/06* (2006.01)

(52) U.S. Cl.
CPC .......... *A61K 31/352* (2013.01); *A61N 5/0624* (2013.01); *C12Q 1/04* (2013.01); *A61N 5/062* (2013.01); *A61N 5/0616* (2013.01)

(58) Field of Classification Search
CPC .... A61K 31/352; A61K 5/062; A61K 31/325; A61N 5/0616; A61Q 1/04
USPC .......................................... 424/9.61; 604/20
See application file for complete search history.

(56) References Cited

U.S. PATENT DOCUMENTS

| | | | |
|---|---|---|---|
| 4,906,100 A * | 3/1990 | Rice et al. ..................... 356/417 |
| 5,860,947 A * | 1/1999 | Stamler ........................... 604/19 |
| 6,290,496 B1 * | 9/2001 | Azar et al. ..................... 433/29 |
| 2002/0183808 A1 * | 12/2002 | Biel ................................. 607/88 |
| 2005/0059731 A1 * | 3/2005 | Albrecht et al. .............. 514/453 |
| 2006/0115440 A1 * | 6/2006 | Arata et al. ..................... 424/65 |
| 2008/0188558 A1 * | 8/2008 | Godal et al. .................. 514/529 |
| 2011/0117025 A1 * | 5/2011 | Dacosta .............. A61B 5/0059 424/9.6 |

FOREIGN PATENT DOCUMENTS

| | | |
|---|---|---|
| JP | A-H7-504699 | 5/1995 |
| JP | A-H7-509236 | 10/1995 |
| JP | 2003531828 A | 10/2003 |
| JP | 2007509034 A | 4/2007 |
| JP | 2007532606 A | 11/2007 |
| JP | 2008502735 A | 1/2008 |
| JP | 2008503557 A | 2/2008 |
| JP | 2008507327 A | 3/2008 |
| JP | 2008526997 A | 7/2008 |
| WO | WO-9319152 A1 | 9/1993 |
| WO | WO-9402022 A1 | 2/1994 |
| WO | WO-0162289 A2 | 8/2001 |
| WO | WO-2005032459 A2 | 4/2005 |
| WO | WO-2005099757 A1 | 10/2005 |
| WO | WO-2005123103 A1 | 12/2005 |
| WO | WO-2006000765 A1 | 1/2006 |
| WO | WO-2006022970 A1 | 3/2006 |
| WO | WO-2006111624 A2 | 10/2006 |

OTHER PUBLICATIONS

Fluorescence and absorption spectra of Rose-Bengal dye in the presence of surfactants, Journal of Luminescence, vol. 22, Issue 4, May-Jun. 1981, pp. 429-439. Abstract only.*
Harrison et al., Copper and Quaternary Ammonium Cations Exert Synergisitic Bactericidal and Antibiofilm Activity against Pseudomonas Aeruginosa, Antimicrobial Agents and Chemotherapy, Aug. 2008, p. 2870-2881.*
Demidova et al., Photodynamic Therapy Targeted to Pathogens, Int J Immunopathol Pharmacol. 2004 ; 17(3): 245-254.*
Chemburu et al., Light-Induced Biocidal Action of Conjugated Polyelectrolytes Supported on colloids, Langmuir Jul. 2008, 24, 11053-11062.*
Dougherty, T.J. et al., Photodynamic Therapy. J. Natl. Cancer Inst. (1998), 90, pp. 889-905.
Wainwright, M., Photodynamic antimicrobial chemotherapy (PACT). J. Antimicrob. Chemother. (1998), 42, pp. 13-28.
Wainwright, M. et al., The Use of New Methylene Blue in Pseudomonas aeruginosa Biofilm Destruction. Biofouling (2002), 18, pp. 247-249.
Ceri et al., The Calgary Biofilm Device: New Technology for Rapid Determination of Antibiotic Susceptibilities of Bacterial Biofilms. J. Clin. Microbiol. (1999) 37, pp. 1771-1776.
Harrison-Balestra et al., A wound isolated *Pseudomonas aeruginosa* grows a biofilm in vitro within 10 hours and is visualized by light microscopy. Dermatol. Surgery, 29(6):631-635, 2003.
Japanese Patent Application No. 2014-242257 Office Action dated Apr. 5, 2016 (English translation is provided).
Canadian Patent Application No. 2,745,059 Office Action dated Oct. 25, 2016.

* cited by examiner

*Primary Examiner* — Michael G Hartley
*Assistant Examiner* — Nabila Ebrahim
(74) *Attorney, Agent, or Firm* — Wilson Sonsini Goodrich & Rosati

(57) ABSTRACT

A composition for use on skin and wounds, comprising a photo-catalyst which is capable of preferentially staining biofilms the composition being for use in the diagnosis and treatment of biofilms in wounds.

17 Claims, 8 Drawing Sheets

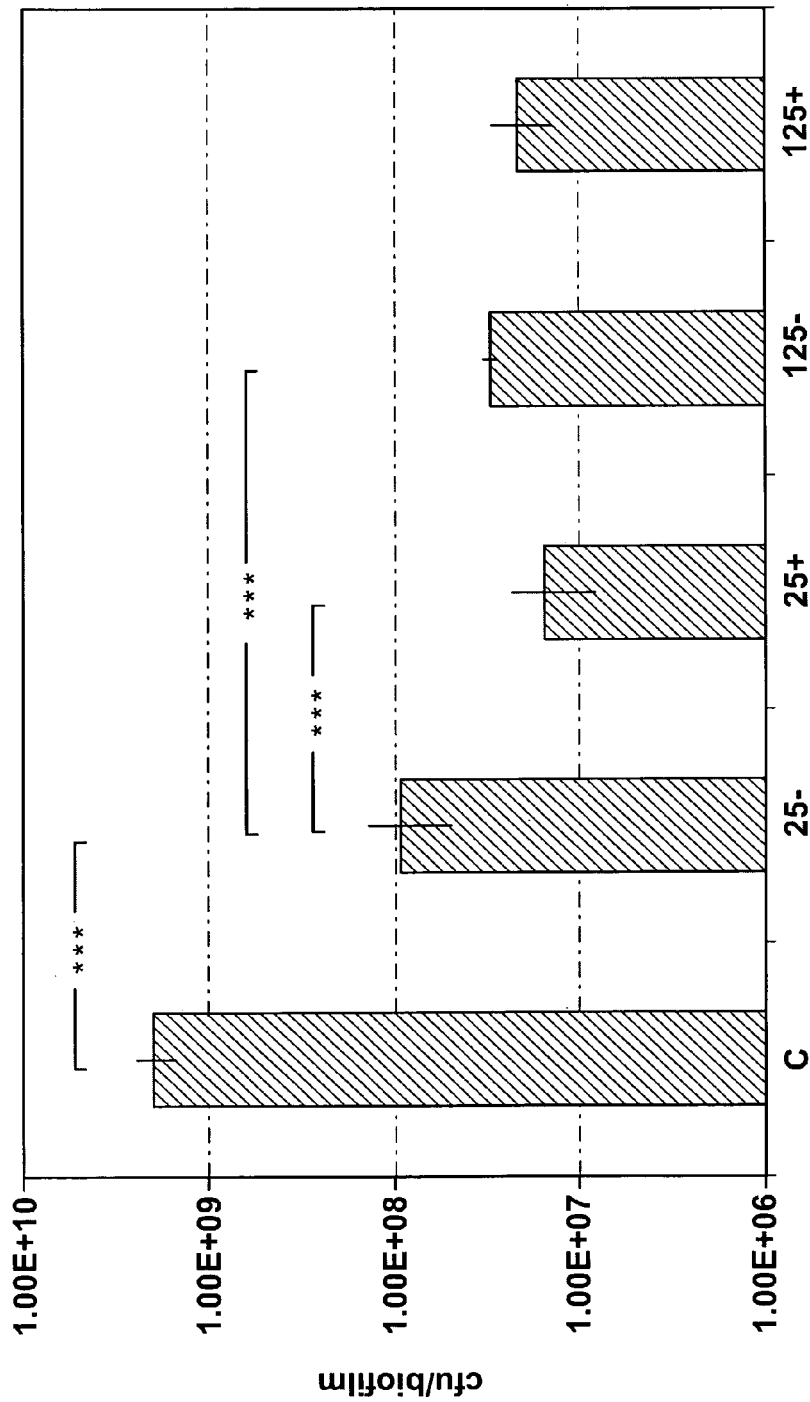
Fig. 1 Rose Bengal PCT of *P. aeruginosa* biofilms. C = control (no photo-catalyst, no light). 25- = 25 µM RB, 4.8 J/cm² light. 25+ = 25 µM RB, 4.8 J/cm² light plus post-treatment rinse step. 125- = 125 µM RB, 24 J/cm² light. 125+ = 125 µM RB, 24 J/cm² light plus post-treatment rinse step. N=4.

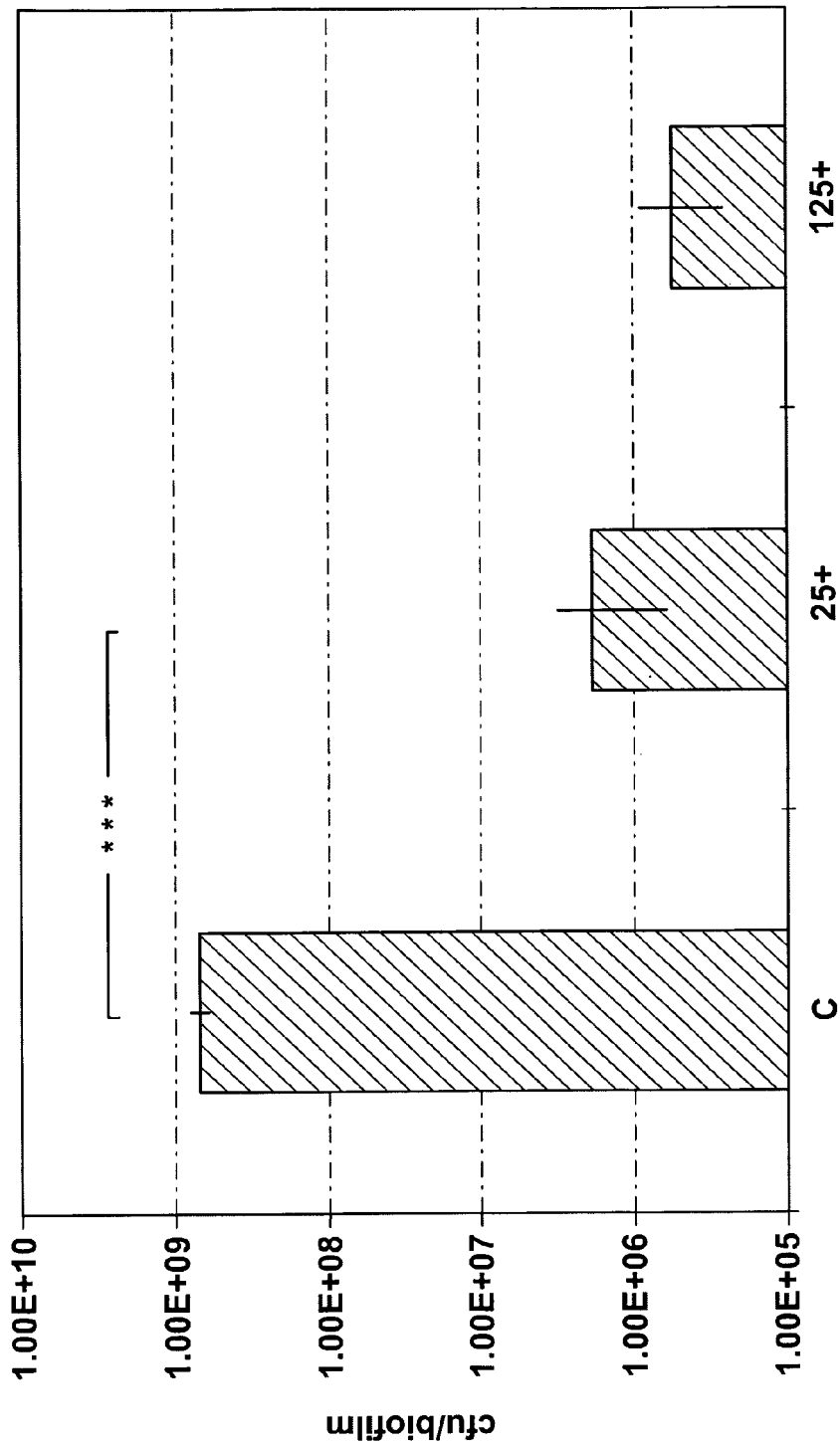
Fig. 2 Rose Bengal PCT of *S. aureus* biofilms. C = control (no photo-catalyst, no light). 25+ = 25 μM RB, 4.8 J/cm² light plus post-treatment rinse step. 125+ = 125 μM RB, 24 J/cm² light plus post-treatment rinse step. N=4.

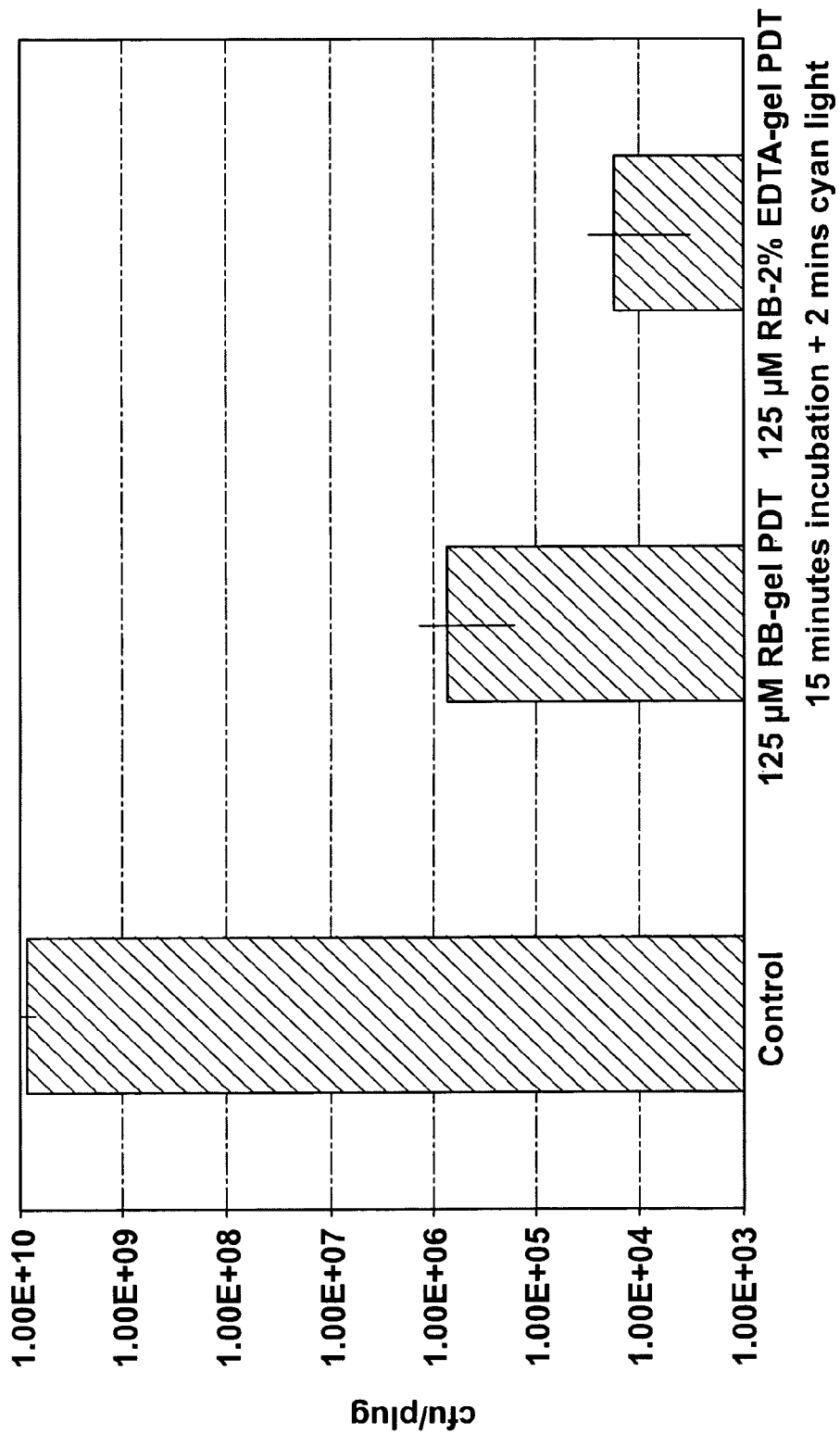
Fig. 3 PCT of *P. aeruginosa* biofilms using 125 μM RB-gel and 125 μM RB-EDTA-gel. N=4.

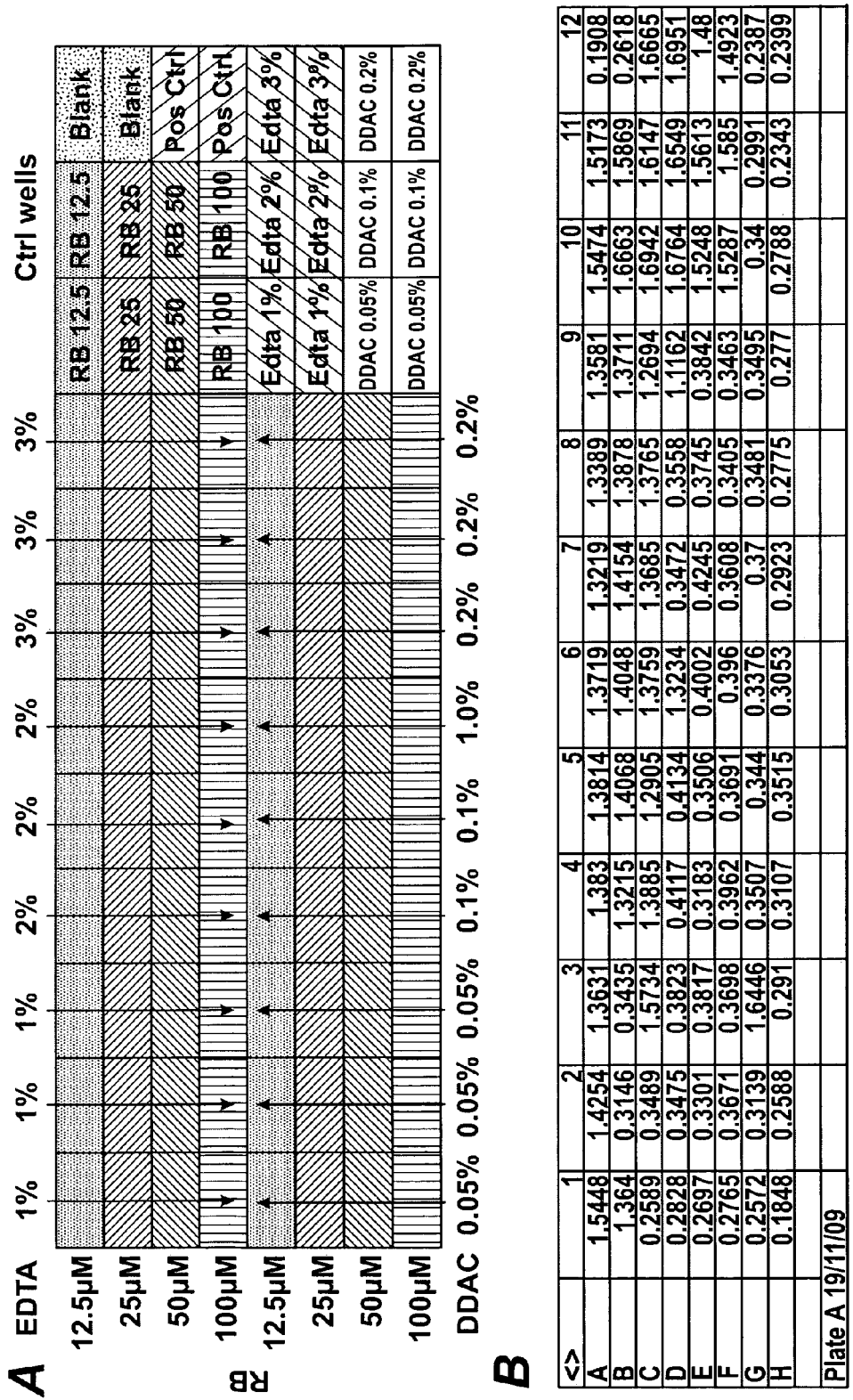
Fig. 4 (A) MBEC assay set-up and (B) results for various combinations of Rose Bengal and EDTA / DDAC with cyan LED light (2 minutes) at pH 5. Values are optical density at 650 nm.

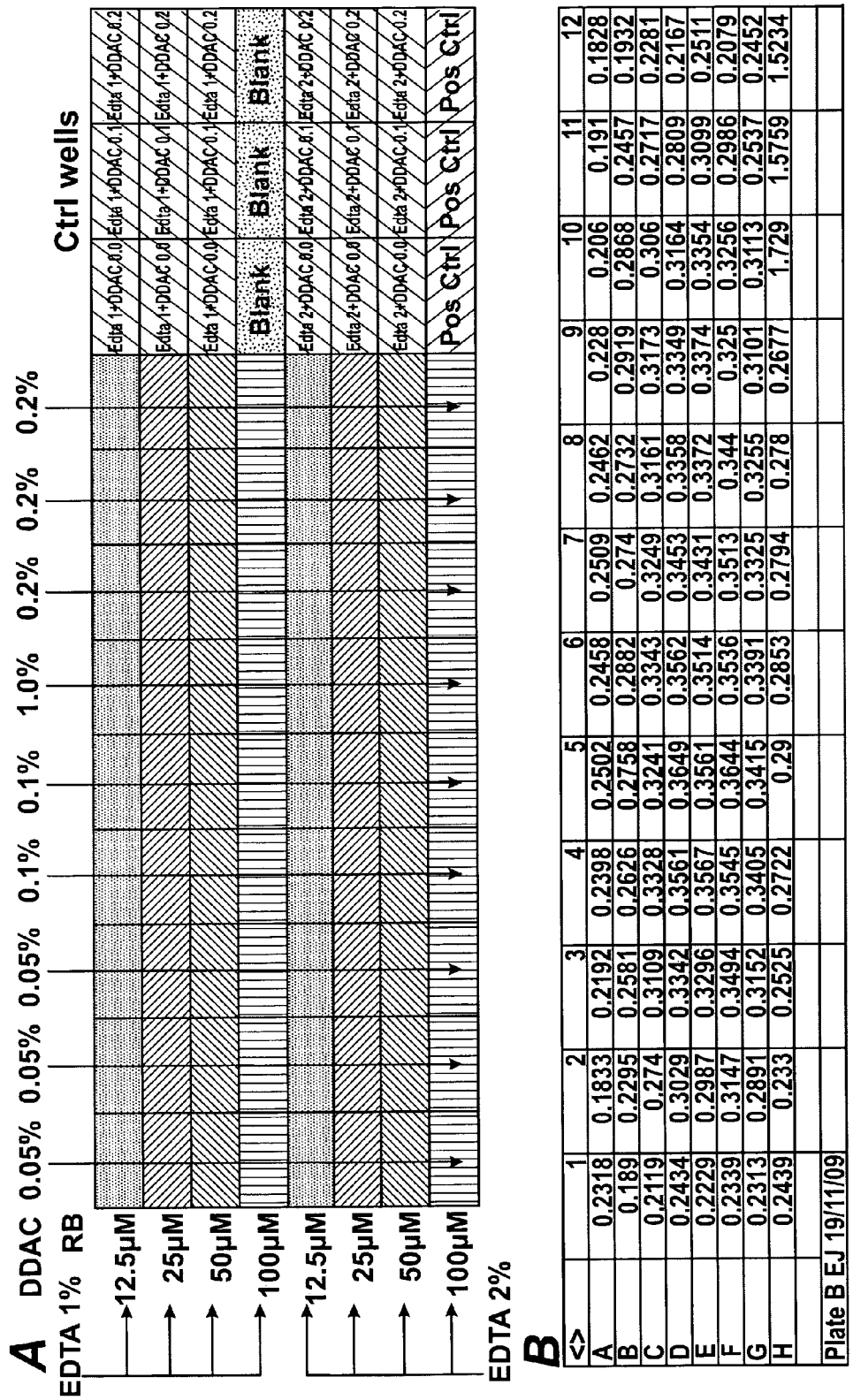
Fig. 5 (A) MBEC assay set-up and (B) automated results for various combinations of Rose Bengal, EDTA and DDAC combined with cyan LED light (2 minutes) at pH 5. Values are optical density at 650 nm.

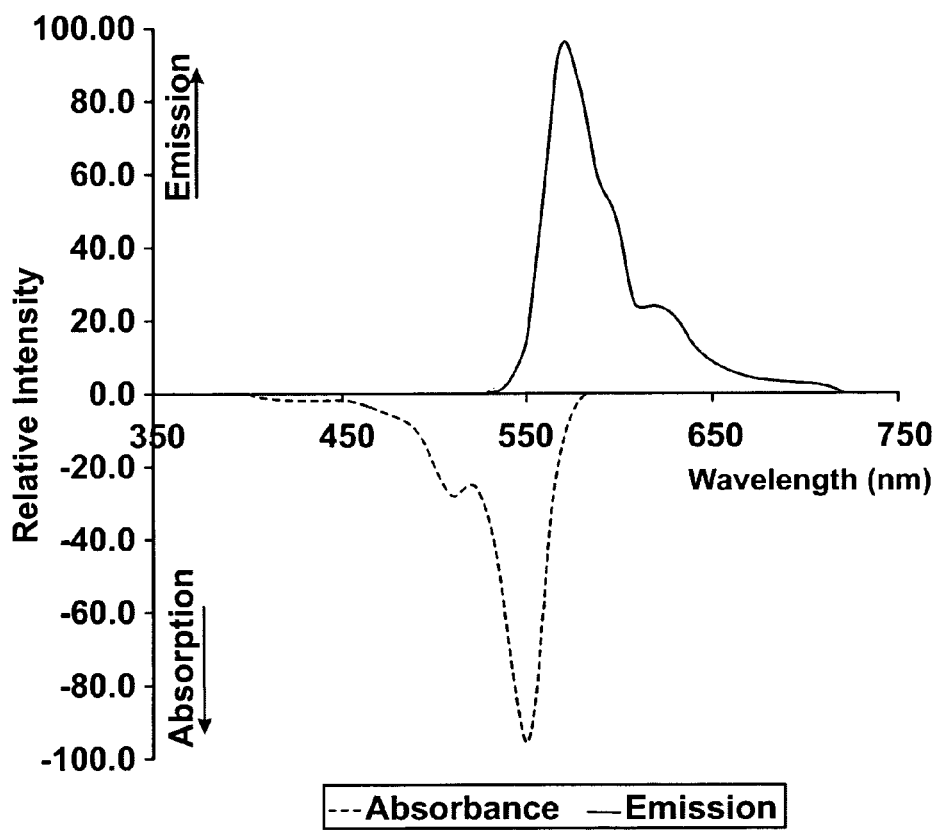
*Fig. 6* Absorption and fluorescence emission spectra of Rose Bengal

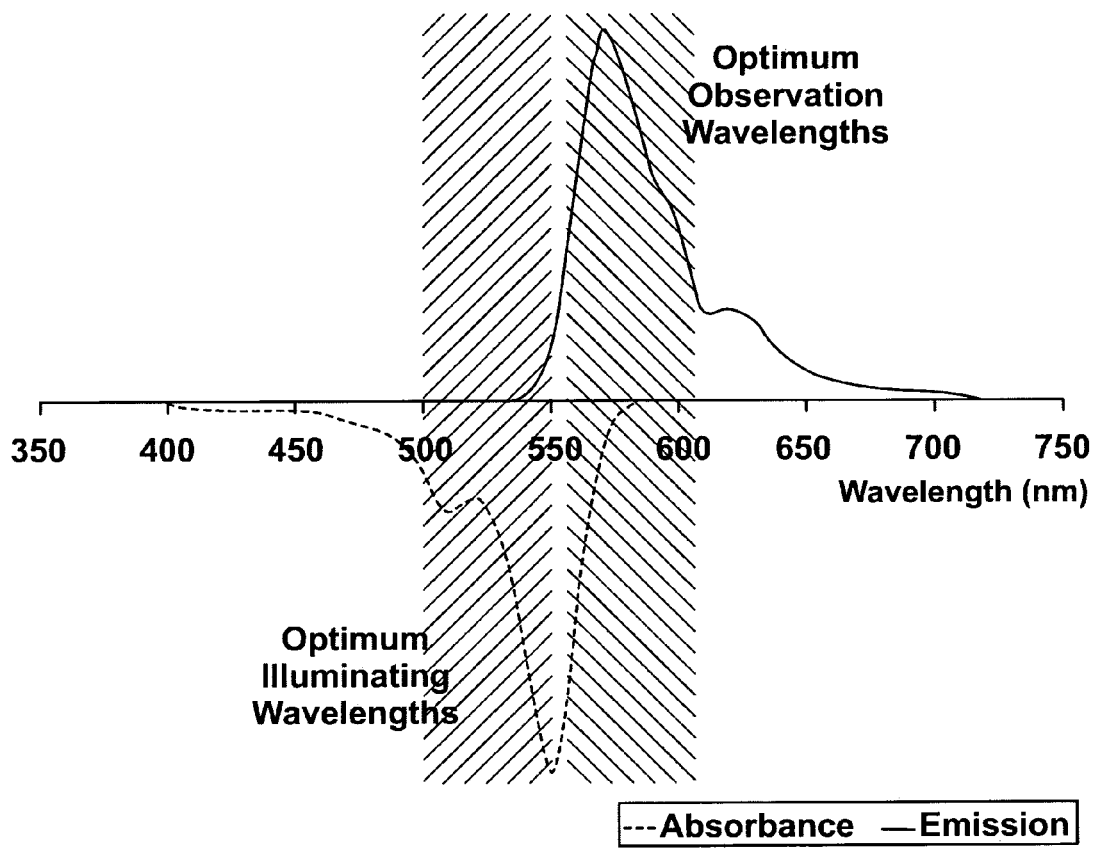
*Fig. 7* Absorption and fluorescence emission spectra of Rose Bengal indicating the preferred illumination and observation wavelengths of the light source and filtered spectacles required for 'reveal' or 'diagnose' mode.

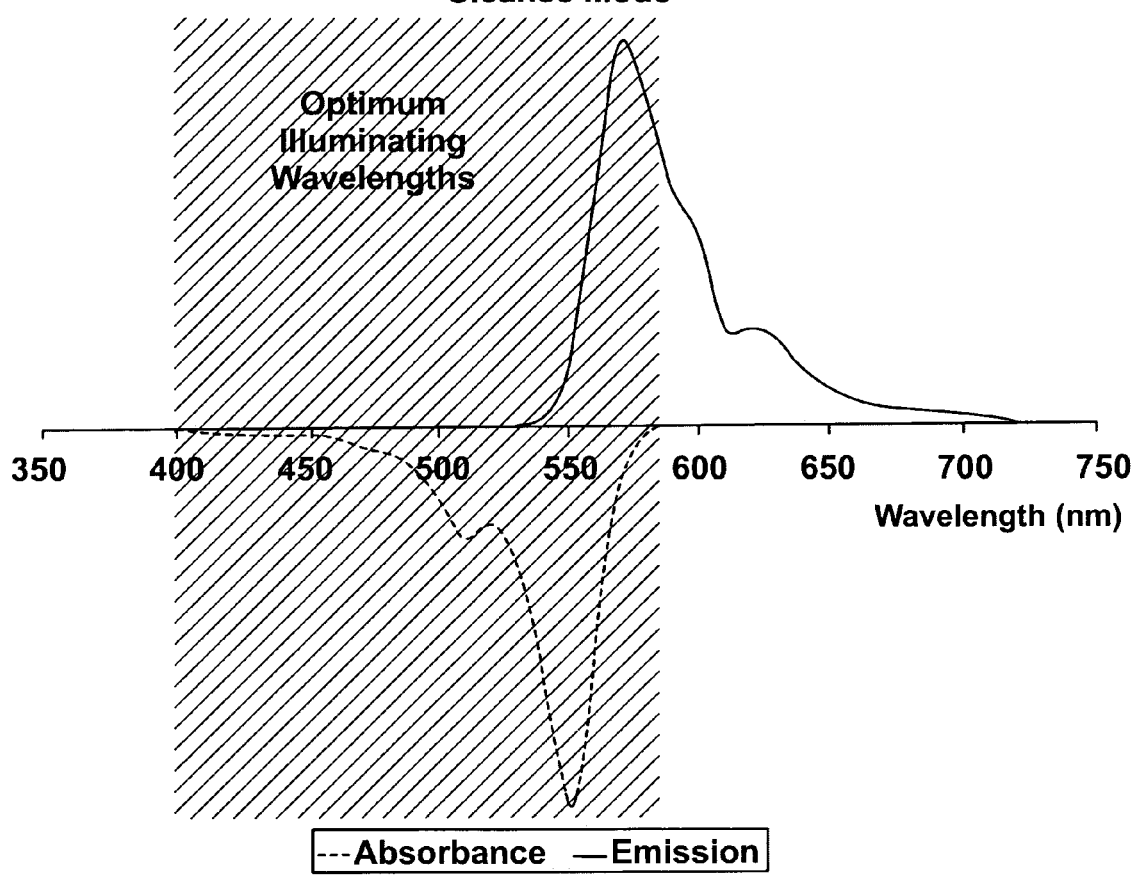
Fig. 8 Absorption and fluorescence emission spectra of Rose Bengal indicating the preferred illumination wavelengths of the light source required for 'activate' or 'cleanse' mode.

ative antimicrobial composition for application to wounds based on such agents. One problem is that these antiseptic agents tend to react with organic materials found in the wound other than the intended microbial targets. This means that to be effective, antiseptic agents need to be included in treatment compositions at high levels, which may cause undesirable side effects with prolonged use such as cell toxicity, hypersensitivity reactions, skin staining and systemic effects.

ANTIMICROBIAL COMPOSITION

This invention relates to a composition which can be applied to skin, wounds, cuts, abrasions or burns for the diagnosis and treatment of bacteria associated with infections. More particularly the invention relates to a composition capable of providing effective antimicrobial activity while at the same time avoiding wound and skin irritation and retardation of wound healing. A further embodiment of the invention relates to a kit for use in the diagnosis and treatment of bacteria associated with infections.

Overuse of antibiotics and the associated increase in bacterial resistance is impacting the efficacy of antibiotics in the treatment of wound infection. Effective alternatives to antibiotics are thus desirable.

Topical antimicrobial materials and preparations containing them have long been recognised as playing an important part in minimising the opportunity for skin and wound infections. Antiseptics are non-selective chemical agents that can be safe to use on living tissue. Molecular iodine, ionic silver and oxidising agents such as sodium hypochlorite and chlorine dioxide have been recognised as antiseptic agents with effectiveness against a wide range of microorganisms. There are however several barriers to making an effective antimicrobial composition for application to wounds based on such agents. One problem is that these antiseptic agents tend to react with organic materials found in the wound other than the intended microbial targets. This means that to be effective, antiseptic agents need to be included in treatment compositions at high levels, which may cause undesirable side effects with prolonged use such as cell toxicity, hypersensitivity reactions, skin staining and systemic effects.

Wounds are often colonised by a variety of microorganisms, some of which may cause infection. It is increasingly recognised that microbial populations living within a biofilm environment contribute to delayed wound healing and infection. Biofilms are comprised of an extracellular matrix that is produced by bacteria once they attach to a surface, and this helps to protect microorganisms from immune cells and antimicrobial agents. Since efficacy of antimicrobial agents (e.g. antibiotics and antiseptics) is compromised by the extracellular biofilm matrix, strategies to disrupt the biofilm and expose microorganisms within can be helpful in increasing the activity level of antimicrobial agents and thus reducing the concentration of such agents needed to make an effective composition.

Biofilms such as those found on teeth in the form of dental plaque, are often easy to visualise with the naked eye due to their thickness, colour and the nature of the substrate on which they are formed. Biofilm visualisation in a chronic or acute wound is not straightforward due to the colours present in the wound and the contents of the wound. Chronic and acute wounds are usually complex in terms of containing dead or devitalised tissue (slough), exudate, pus, blood, medicaments, dressing components, in addition to bacteria and possible biofilm. As such it may be difficult to diagnose the presence of a biofilm in a wound as the visualisation of wound biofilms by the naked eye is difficult. There is thus a need for a means to aid diagnosis of the biofilm for instance by a composition which is able preferentially stain wound biofilms so that they can be visualised. Once visualised, the biofilm can be treated appropriately.

Photodynamic therapy (PDT) is a form of treatment used in cancer therapy that selectively destroys tumour cells while sparing healthy cells (Dougherty T. J., Gomer C. J., Henderson B. W., Jori G., Kessel D., Korbelik M., Moan J. & Peng Q. (1998). Photodynamic Therapy. J. Natl. Cancer Inst. 90, 889-905). A dye photosensitizer or photo-catalyst is typically applied to target cells and then illuminated with light of an appropriate wavelength to activate the photo-catalyst. The activated photo-catalyst then transfers energy to surrounding molecules to create active radicals and reactive oxygen species, such as singlet oxygen, which cause cell death. This principle has also been employed in recent years to kill bacteria (Wainwright M. (1998). Photodynamic antimicrobial chemotherapy (PACT). J. Antimicrob. Chemother. 42, 13-28) and destroy biofilms. (Wainwright M., Phoenix D. A., Nickson P. B. & Morton G. (2002). The Use of New Methylene Blue in *Pseudomonas aeruginosa* Biofilm Destruction. Biofouling, 18, 247-249).

Surprisingly we have found that it is possible to preferentially stain biofilms in wounds by the use of a composition comprising a photo-catalyst which discloses the biofilm. If biofilm is found to be present, the photo-catalyst can then be illuminated to activate it to catalyze the formation of singlet oxygen and radicals to kill the biofilm bacteria and disrupt the structure of the biofilm.

Accordingly a first aspect of the invention provides a composition suitable for use on skin and wounds comprising a photo-catalyst which is capable of preferentially staining biofilms the composition being for use in the diagnosis and treatment of biofilms in wounds.

By preferentially staining it is meant that the photo-catalyst selectively binds to the biofilm rather than the host tissue. In this way, the photo-catalyst can be used simply to diagnose the biofilm by disclosing the biofilm or to diagnose and then destroy the biofilm. The photocatalyst becomes bound to extracellular biofilm matrix molecules as well as being bound to and/or taken up by the biofilm bacteria cells rather than the tissue of the wound. Preferably the staining of the biofilm by the photo-catalyst diagnoses the biofilm by disclosing it to make it visible to the naked eye. For some photo-catalysts the stained biofilm can be made to fluoresce for instance by illumination with a light source. The fluorescence can make the stained biofilm more visible. The light source is selected to emit light of an appropriate wavelength such that the photo-catalyst absorbs light energy in the form of photons to excite the photo-catalyst and cause it to fluoresce. The observation of fluorescence may be enhanced using appropriate optical filters which exclude non-fluorescent wavelengths for the photo-catalyst, for instance in the form of spectacles with optical filters.

The compositions according to a first aspect of the invention comprise one or more photo-catalysts capable of preferentially staining biofilms. The photo-catalyst is capable of generating singlet oxygen by photo catalytic energy transfer. The photo-catalyst preferably generates a level of light-dependent toxicity that kills biofilm bacteria and breaks down the extracellular biofilm matrix structure but does not deleteriously affect host cells. Preferably the photo-catalyst is a water soluble dye that absorbs light in the visible region, can produce sufficient fluorescence for detection and can produce singlet oxygen. Suitable photo-catalysts may be azo dyes (Congo Red, Bismark Brown, Allura Red), chlorins (benzoporphyin derivatives, porphines, meso-tetra porphines, chlorin e6), chlorophylls (chlorophylls, bacteriochlorophylls, protochlorophylls), coumarins (thiocoumarin, 3-benzoyl-7-methoxycoumarin, khellins, psalorens), metallophthalocyanines (aluminium phthalocyanines, zinc phthalocyanines), metalloporphyrins (zinc porphyrazines), naphthalocyanines (zinc naphthalocyanine) perylenequinones (hypericins, hypocrellins, Calphostin C), phenazines (Neutral Red), phenothiaziniums (methylene blue, toluidine blue O), phenoxaziniums (brilliant Creysyl Blue), pheophorbides (sodium pheophorbide), pheophytins (bacteriopheophytins), porphycenes (tetra-n-propyl-porphycene), porphyrins (hematoporphyrins, Photofrin®, protoporphyrins, 5-amino levulinic acid), purpurins (octaeythlpurpurin), tetrapyrroles (dihydro-tetrapyrroles, trihydro-tetrapyrroles), thiophenes (terthiophenes, bithiothenes), triarylmethanes (Patent blue, brilliant blue, Fast Green), and most preferably xanthenes (eosin, erythrosine, Rose Bengal). Most preferably the photo-catalyst is a phenothiazinium or a xanthene.

Preferably the photo-catalyst absorbs maximally in the visible region, more preferably 400 to 700 nm (white light) and even more preferably 510 to 570 nm (blue-green light) (e.g. Rose Bengal absorbs maximally at 550 nm, erythrosine at 526 nm) as this makes a wide range of light sources suitable for use with the composition of the invention or for inclusion in the kit of the invention.

Preferably the photo-catalyst produces sufficient fluorescence for detection.

Photo-catalysts suitable for use in compositions of the invention are most preferably selected from those giving high quantum yields (or relative efficiencies) for example greater than 0.2 of triplet formation and singlet oxygen generation with acceptable fluorescence (sufficient for detection) for example greater than 0.01. Accordingly, most preferred are xanthenes such as eosin (fluorescence 0.20-0.63; singlet oxygen 0.37-0.60), erythrosine (fluorescence 0.02-0.08; singlet oxygen 0.62-0.69) or Rose Bengal (fluorescence 0.018-0.08; singlet oxygen 0.75-0.86). Rose Bengal is 4,5,6,7-Tetrachloro-3',6'-dihydroxy-2',4',5',7'-tetriodo-3H-spiro[isobenzofuran-1,9'-xanthen]-3-one.

The photo-catalyst is preferably included in the composition at a level of from 0.0001% to 1% by weight, more preferably 0.0025% to 0.025% by weight, even more preferably 0.0025% to 0.01% by weight.

The compositions of the present invention may be in a form that lightly adheres to tissues and may be readily rinsed away after a short duration to aid visualisation of the stained biofilm. A viscous fluid, for instance a gel, gives the advantage of flow into the wound to form an intimate contact with the wound bed. Preferably the gel has a high enough viscosity that it does not flow out of wounds on areas of the body that are or become non-horizontal. Preferably the gel has a viscosity in the range of 100,000 to 800,000 cP, more preferably 300,000 to 500,000 cP.

The composition may also comprise a viscosifier such as a cellulose derivative such hydroxyethyl cellulose (HEC), carboxymethyl cellulose or hydroxypropyl cellulose; gums; sugar/alcohol derivatives such as glycerol, sorbitol, maltitol, mannitol, maltodextrin or polydextrose; natural polymers such as gelatin, pectin, chitosan or alginate; synthetic polymers such as carbopol, polyvinylpyrrolidone, polyvinyl acetate, polyvinyl alcohol, polyacrylate, polymethacrylate, polyethylene glycol or poloxamers. Preferably the composition comprises from 1 to 5% by weight of a viscosifier and most preferably HEC.

The composition of the invention may also comprise a humectant such as propylene glycol (PG), glycerol, polyethylene glycol, polydextroe, sorbitol, triethanlolamine, cyclomethicone, ammonium lactate or glycerol ester. Preferably the composition comprises from 5% to 15% by weight of a humectant and most preferably PG.

The composition of the invention may also comprise a metal chelating agent such as ethylene diamine tetracetic acid (EDTA), citric acid, deferasirox, deferiprone, deferoxamine, deferazoxane, ethylene glycol tetraacetic acid, gluonic acid, nitrilotriacetic acid or trisodium citrate at a level of 0.1 to 2.0% by weight, or an agent to assist penetration of the photocatalytic agent into the biofilm such as a surfactant and in particular a cationic quaternary ammonium surfactant such as dialkyl dimethyl ammonium chloride or alkyl pyridinium chloride benzalkonium chloride, benzethonium chloride or an alkyl trimethyl ammonium chloride at a level of 0.1 to 1.0% by weight.

Preferably the composition of the invention has a pH in the range of from 5 to 7 and most preferably around 5.5.

Preferably the composition of the invention is in the form of a gel and comprises a viscosifier such as HEC, a humectant such as PG, a metal chelator such as EDTA, a surfactant such as DDAC and water and in particular 2.0% w/v hydroxyethylcellulose, 10.0% w/v propylene glycol, 0.5% EDTA, 0.1% DDAC and approximately 87% v/v sterile, distilled water. Alternatively, the compositions of the present invention could be in the form of a solution applied to the wound from a syringe, sachet, spray, aerosol or brush or a gel sheet.

To make a gel composition of the invention, the photo-catalyst is incorporated from a stock solution in order to achieve a gel of required photo-catalyst concentration (from 0.0001% to 1%).

The composition of the present invention will be used primarily on wounds which show signs of clinical infection (inflammation, malodour, exuding, hypoxic, etc.), may be at risk of infection, appear to have slough or biofilm present, or are generally recalcitrant. The composition could also be used at dressing change, in order to detect and reduce biofilm, and also to monitor the efficacy of the treatment regime and direct future treatment.

A further aspect of the present invention relates to a kit of parts for use in the diagnosis and treatment of biofilm in wounds comprising:

a composition comprising a photo-catalyst which preferentially stains biofilms; and a light source capable of activating the photo-catalyst to fluoresce so that the biofilm is diagnosed, and capable of generating light-dependent toxicity that kills bacteria and breaks down the biofilm structure.

The light source may be chosen to emit wavelengths of light that correspond to the absorption characteristics of the photo-catalyst. The light must be of sufficient power at the appropriate wavelengths that the distance away from the target and the duration of illumination are sufficient that the required energy dose is received by the target. These parameters are linked by the following equation at a given distance from the target:

$$\text{Energy dose (J/cm}^2\text{)}=\text{power (W/cm}^2\text{)}\times\text{time (seconds)}$$

That is, by increasing the power of the light source one can reduce the required illumination time for a required energy dose, or increase the energy dose received by the sample for a fixed duration.

More preferably, the light source has two modes; 'reveal' or diagnose' mode (light wavelength causes the photo-catalyst to fluoresce) and a second, preferably higher-power setting in 'activation' or 'cleanse' mode (wavelength causes the photo-catalyst to become activated and transfer energy to surrounding molecules, generating radicals and reactive oxygen species, such as singlet oxygen, to kill the bacteria and breakdown the biofilm structure). Discrete wavelength bands can be used for 'reveal' or 'diagnose' mode. There is preferably no overlap between the illumination stage (regions up to the $\text{Abs}_{max}$ but not overlapping significantly into emission wavelengths) and subsequent observation of fluorescence (regions of greatest emission). For 'activation' or 'cleanse' mode the wavelengths should correspond with the regions of greatest absorption for the photo-catalyst in use. The wavelength bands are illustrated for Rose Bengal in FIGS. 7 and 8. The light source preferably has an optical system which is capable of filtering light wavelengths so that the source can operate in two modes, a first mode in which the source only produces light wavelengths in the region 300 nm to 10 nm below the absorption maxima ($Abs_{max}$) of the photocatalyst to enable the biofilm to be diagnosed and a second mode in which the source only produces light wavelengths in the region of a band 75 nm above and 75 nm below the $Abs_{max}$ of the photocatalyst to enable the biofilm to be treated. More preferably in the diagnosis mode the source only produces light wavelengths in the range of 50 nm below the $Abs_{max}$ to 10 nm below the $Abs_{max}$, and most preferably only 30 nm below to 10 nm below the $Abs_{max}$. More preferably in treatment or cleansing mode, the light source only produces light wavelengths 40 nm either side of the $Abs_{max}$.

The light source may be a white light source such as tungsten, halogen or pulsed xenon lamp that is passed through a "short pass" filter such as Schott Glass BG3 or BG25. Preferably the light source is a narrow spectrum source that does not require filtering or attenuation such as a blue light emitting diode such as Luxeon, type LXHL-NB96 or 97 from Lumileds Lighting LLC. The light source may be multiple use or fully disposable.

Preferably the kit further comprises a wound irrigation solution for rinsing the wound before illumination with the light source in diagnosis mode or after illumination after cleansing or treatment or both. Preferably the kit further comprises diagnostic spectacles for use in diagnosing the biofilm wherein the spectacles contain a filter to exclude all wavelengths of light below the $Abs_{max}$ of the photo-catalyst. In this way the user is assisted in visualising the fluorescence of the photocatalyst present in the biofilm. More preferably the spectacles filter is efficient at transmitting wavelengths of light corresponding to the fluorescence emission spectra of the photocatalyst. The spectacles can be multiple use or fully disposable. The spectacles filter is for example Schott glass OG550, Hoya OG560 or Uvex Laservision p1008.

The composition present in the kit may comprise a first photo-catalyst used to diagnose the biofilm and second photo-catalyst used to treat the biofilm. For example the photo-catalyst used for diagnosis may be a xanthene such as erythrosine or Rose Bengal and the photo-catalyst used for treatment may be a phenothiazinium such as methylene blue or toluidine blue. Accordingly, the 'reveal' or 'diagnose' mode of the light source may be specific to a photo-catalyst such as Rose Bengal and the 'activation' or 'cleanse' mode of the light source may be specific to a second photocatalyst such as methylene blue.

In an example of a typical treatment, a composition according to the invention is applied to the whole wound or desired regions in order to achieve a thin but consistent layer of composition for instance 0.1 to 0.5 cm in thickness. The composition is left in place for 0.5 to 15 minutes, more preferably 1 to 5 minutes. Prior to any illumination, the gel can be left in place or more preferably excess gel is rinsed away from the wound using sterile water, saline, or a suitable wound irrigation solution.

The wound is then inspected for presence of preferentially stained biofilm. This may be done with the naked eye or the wound can be illuminated with a light source at a distance in the range of 0 to 20 cm. Preferably the light source is at a distance of 10 cm. The light source is selected to emit wavelengths in the region 300 nm to 10 nm below the maximal absorption wavelength ($Abs_{max}$) of the photo-catalyst. This causes the photo-catalyst in the stained biofilm to fluoresce. Preferably the user wears diagnostic spectacles to observe the wound. The spectacles have a light filtration system which excludes wavelengths of light below the $Abs_{max}$ of the photo-catalyst and allows any fluorescence to be seen remarkably clearly.

If fluorescence is seen, then biofilm is present in the wound and optionally the user may decide that treatment or "cleansing" is necessary to kill the bacteria and breakdown the biofilm structure. To cleanse the wound of biofilm the wound is illuminated from a distance of around 10 cm with a light source that has intense light in the band 75 nm below and 75 nm above the $Abs_{max}$ of the photo-catalyst for a period of 10 seconds to 5 minutes. The wound may then optionally be rinsed with an irrigation solution to remove dead bacteria and disrupted biofilm. The wound can then be dressed.

Typically, treatment should take place at subsequent dressing changes to monitor reduction of the biofilm. The wound can be further inspected for presence and reduction of biofilm—with the naked eye or with the light source in 'reveal' or 'diagnosis' mode again. If the wound is large and/or heavily colonised with biofilm, a further round of gel application and cleansing treatment may be beneficial. The wound can then be dressed with an appropriate primary and secondary dressing.

The following is a brief description of the figures and tables:

FIG. 1 shows Rose Bengal Photo-Catalytic Therapy of *P. aeruginosa* biofilms;

FIG. 2 shows Rose Bengal Photo-Catalytic Therapy of *S. aureus* biofilms;

FIG. 3 shows Photo-Catalytic Therapy of *P. aeruginosa* biofilms using Rose Bengal gel containing EDTA;

FIG. 4 shows the assay set-up and results for optimising a Photo-Catalytic Gel formulation;

FIG. 5 shows the assay set-up and results for further optimising a Photo-Catalytic Gel formulation;

FIG. 6 shows the absorption and fluorescence emission spectra of Rose Bengal;

FIG. 7 shows the preferred illumination and observation wavelengths for the light source and spectacles for "reveal" or "diagnose" mode; and FIG. 8 show the preferred illumination wavelengths of light required for "activate" or "cleanse" mode.

The following examples are illustrative of the present invention.

EXAMPLE 1

Photo-Catalytic Therapy of Bacterial Biofilms Using an In vitro Wound Biofilm Model $1 \times 10^4$ *P. aeruginosa* or *S. aureus* cells in 50% Muller-Hinton Broth: 50% Foetal Calf Serum were inoculated into 14 mm bore holes made in gamma-irradiated, sterile pork belly pieces and incubated for 48 hours at 37° C. Before treatment, biofilm-containing pieces were rinsed once by placing the pieces with sterile forceps into a 100 ml volume of 0.85% saline for 1 minute to remove loosely-adhered cells. In the case of *P. aeruginosa*, biofilms appeared to have spread from the central area of inoculation throughout the bore holes and onto the skin. Biofilms were also pigmented blue-green in parts, due to the production of pigment pyocyanin. In contrast, *S. aureus* biofilms were apparent only on closer inspection, did not appear to have spread outside the bore holes and were not coloured. Pieces were then placed into a solution of 25 µM or 125 µM Rose Bengal in sterile distilled water for 15 minutes. Following removal it was apparent that biofilms had preferentially been stained by Rose Bengal in comparison to areas of sterile flesh and skin which were not colonised, such as the extreme edges and sides of the pieces. Stained pieces were placed 5 cm under the Bioptron Compact III light source for 120 or 600 seconds illumination (approximately 4.8 or 24 J/cm$^2$ in the region of maximal absorption by Rose Bengal, 550 nm). Following PCT, samples were either: (a) prepared for serial dilution and viable counting on agar by sterile swabbing then stomaching; or (b) given a post-treatment rinse step in maximal recovery diluent (MRD) containing 0.01% Tween-80 (to determine if PCT had an effect on biofilm structure) then prepared as in (a).

Following 25 µM RD PCT, the post-treatment rinse step gave significantly increased reductions in *P. aeruginosa*, where biofilm removal was enhanced to 2 log. (compare FIG. 1, bars 2 & 3). In terms of pure *P. aeruginosa* biofilm bacteria cell killing, increasing the RB and light dose five-fold resulted in a significantly increased reduction, indicating a clear dose-response (compare FIG. 1, bars 2 & 4).

The post-treatment rinse step was maintained in the treatment of *S. aureus* biofilms. A dose-response relationship was observed where the higher doses of RB and light increased biofilm cell reductions to over 3 log$_{10}$, but compared to the lower dose this was not statistically significant (compare FIG. 2, bars 2 & 3).

Using a challenging biofilm model, it was demonstrated that biofilms of two bacteria commonly found in infected wounds, *P. aeruginosa* and *S. aureus*, could be stained preferentially over uncolonised areas of sterile flesh and skin. The stained biofilms were subsequently shown to be highly susceptible to RB PCT using low doses of photo-catalyst and light, in a dose-dependent manner as demonstrated by biofilm disruption and viable count reduction.

EXAMPLE 2

Uptake of Photo-catalyst by Biofilms as Measured by Colorimetric Spectroscopy

This method aimed to measure bulk photo-catalyst uptake by biofilm by measuring the colour intensity of stained samples.

*P. aeruginosa* biofilms were cultured in the Constant-Depth Film Fermenter (CDFF) for 5 days. Briefly, biofilms were formed in recesses in 15 pans around the rim of a rotating steel turntable onto which inoculum or sterile media was allowed to steadily drip. A scraper bar distributed inoculum or media over the pans as the turntable rotated, maintaining the biofilms at a steady depth. Each pan contained 5 removable plugs, 4 mm in diameter which were recessed to a depth of 300 µm. The resulting biofilms were reproducible in terms of appearance and microbiological composition and could be removed from the CDFF through a sampling port using sterile instruments. In duplicate, biofilm-containing pans were removed from the CDFF and either stained by immersion into a 125 µM solution of Rose Bengal in saline for 10 minutes, or were simply rinsed in sterile saline for the same duration. Biofilm pans were then placed directly beneath a SpectroEye colour spectrophotometer. The sample reading platform was precisely the same dimension as the stained biofilms (5 mm in diameter). Green-red shift values were measured automatically in triplicate by the SpectroEye, i.e. the more RB taken up, the larger the red shift. A standard curve of RB under the SpectroEye was also prepared (adjusted for the green-red shift contributed by non-stained biofilms;) ($R^2$=0.98) and used to determine the concentration of RB contained within the biofilms after the 10 minute incubation period.

| Sample | a* (green-red shift) value (arbitrary units) | RB (µM) contained in biofilm | Mean uptake (µM) |
|---|---|---|---|
| 1 | 49.23 | 136.48 | 124.6 ± 9.6 |
| 2 | 43.77 | 120.85 | |
| 3 | 40.36 | 111.10 | |
| 4 | 48.71 | 134.99 | |
| 5 | 44.85 | 123.95 | |
| 6 | 43.53 | 120.17 | |

After 10 minutes of incubation in the 125 µM RB solution, the biofilms were determined to contain on average a concentration of 125 µM RB, as determined by comparison with standard curve with control biofilm green-red values subtracted. This suggests that the biofilms efficiently take up the RB stain (mean uptake was the same as the concentration of RB used).

These findings suggest that incubation of biofilms need only occur for 10 minutes maximum for optimal uptake of RB from solution. Incorporation of biofilm-permeating agents may enhance or speed up this uptake process.

EXAMPLE 3

Enhancement of Photo-Catalytic Therapy by EDTA Incorporation into a Photo-Catalytic Gel Using a Specialised Light Source

*P. aeruginosa* biofilms were cultured in a CDFF for 5 days as detailed in Example 2. Photo-catalytic gels were prepared using 2% w/v hydroxyethyl cellulose, 10% w/v propylene glycol and purified water as the gel base. To one gel, a volume of 1 mM Rose Bengal in sterile water was added to give a RB-gel containing 125 µM RB. To the other gel a similar volume was added along with 2% w/v ethylene diamine tetraacetic acid (EDTA) to give RB-EDTA-gel. Photo-catalytic therapy was applied to biofilm samples using a 15 minute dark incubation period with either gel, a rinsing step in sterile saline to remove excess gel, two minutes of light from a distance of 10 cm followed by a post-treatment rinse. The light source used was a cyan light-emitting diode (LED) Luxeon, type LXHL-NE96 (Lumileds Lighting LLC). Untreated controls were only subjected to a rinse step. FIG. 3 shows how PCT using RB-gel and cyan LED gave 4 log kills of *P. aeruginosa* biofilms, which is significantly greater than the 2-3 log kills seen with previous, non-optimal light sources. PCT using the RB-EDTA-gel enhanced biofilm cell killing by a further 1.5 log compared to RB-gel PCT. This potentiation of the photo-catalytic effect by EDTA may be due to the chelation of metal ions from the biofilm structure, the effect on Gram-negative bacterial cell membranes, or both, which may lead to increased uptake of photo-catalyst by the biofilm (staining) and biofilm cells.

EXAMPLE 4

Visualising Biofilm Staining Using Blue Light and Biofilm Diagnostic Spectacles

Overnight stationary phase cultures of *P. aeruginosa* or *S. aureus* were diluted 1-in-30 in a 50:50 solution of Muller-Hinten broth and fetal calf serum. Small pieces of steak meat, approximately 1 cm×4 cm×4 cm were prepared from defrosted meat using sterile scalpels and scissors. The pieces were sterilized by aseptically immersing them into analytical grade ethanol and mixing for 5 seconds, followed by a 5 second rinse in sterile saline, then placed into sterile 15 cm diameter Petri dishes. Samples were gently padded dry with sterile, lint-free wipes. To the centre of each meat sample, 10 µl volumes of P. aeruginosa or S. aureus suspensions were added, then the Petri lid dish covered in parafilm. Dishes were incubated overnight at 37° C. to allow biofilms to form.

A dish containing three samples of P. aeruginosa biofilms was used to demonstrate the ability of RB-gel to stain biofilms. Biofilms could be observed with the naked eye against the red-brown meat colour, but they were not immediately obvious. One of the three biofilm-containing pieces was randomly assigned to be the treated piece. A volume of 125 µM RB-EDTA-gel was added to the meat piece in order to cover the whole of the piece. After 15 minutes the gel was rinsed off as efficiently as possible using syringes of sterile saline and Pasteur pipettes.

The three pieces were then observed firstly under a blue LED (Luxeon, type LXHL-NE96, Lumileds Lighting LLC), then under the blue light with Biofilm Diagnostic Spectacles (Uvex Laservision P100). Under the blue light with the room lighting dimmed all three pieces of meat looked similar; that is there was no indication of any biofilm present on any piece, nor were there any stained areas visible. When wearing the diagnostic spectacles the user was immediately able to distinguish between the stained biofilm-containing piece and the non-stained pieces. The non-stained pieces did not have any fluorescing regions and only a slight sheen where the biofilms were known to exist was indicative of their presence. This is in dramatic contrast to the piece containing the stained biofilm. Here, the diagnostic spectacles allowed the visualisation of the fluorescing, stained biofilm. The region containing the biofilm was visible as a vivid orange colour, remarkably distinct from surrounding tissues which were not stained. It was possible to distinguish the shape and thickness of biofilm present by the intensity of the fluorescence.

EXAMPLE 5

Photo-catalytic Anti-biofilm Delivery Vehicle Formulation Using Minimum Biofilm Eradication Concentration (MBEC) Method Using the MBEC method, previously developed by The University of Calgary as the Calgary Biofilm Device (Ceri H., Olson M. E., Stremick C., Read R. R., Morck D. & Buret A. (1999). The Calgary Biofilm Device: New Technology for Rapid Determination of Antibiotic Susceptibilities of Bacterial Biofilms. J. Clin. Microbiol. 37, 1771-1776.), various combinations of photo-catalyst, metal chelators and surfactant in sterile water were tested for their ability to eradicate P. aeruginosa biofilms with suitable illumination from a cyan LED lamp.

FIG. 4 shows how EDTA potentiates the action of RB and light in a concentration-dependent manner against biofilms of P. aeruginosa (A-D 1-9 compared to A-D 10-11). This could be due to EDTA chelating metals from the biofilm structure and from the Gram-negative outer membrane of P. aeruginosa, enhancing the uptake and therefore photo-catalytic action of RB. Clear synergy between RB and EDTA was therefore demonstrated. FIG. 4 also shows that DDAC also potentiates the action of RB and light in a concentration-dependent manner against biofilms. FIG. 5 demonstrates how all three agents act synergistically against P. aeruginosa.

EXAMPLE 6

Illustration of the Preferred Wavelengths Required for 'Diagnosis' and 'Cleanse' Mode The absorption and fluorescence emission spectra of Rose Bengal (FIG. 6) were used to graphically illustrate the preferred wavelengths of light required for the present invention. FIG. 7 shows how discrete wavelength bands can be used for 'reveal' or 'diagnose' mode. There is preferably no overlap between the illumination stage (regions up to the $Abs_{max}$ but not overlapping significantly into emission wavelengths) and subsequent observation of fluorescence (regions of greatest emission). FIG. 8 shows how for 'activation' or 'cleanse' mode the wavelengths should correspond with the regions of greatest absorption.

The invention claimed is:

1. A composition for diagnosis and treatment of biofilms in or on wounds, comprising 0.05% to 1.0% by weight of a cationic quaternary ammonium surfactant, 0.1% to 3.0% by weight of a metal chelating agent, and a photo-catalyst which is capable of preferentially staining biofilms, wherein the photo-catalyst comprises Rose Bengal, wherein the amount of Rose Bengal present in the composition is from 0.0025% to 0.025% by weight such that the composition is able to diagnose and treat biofilms in or on wounds.

2. The composition as claimed in claim 1 characterised in that the photo-catalyst preferentially stains the biofilm by binding to the biofilm.

3. The composition as claimed in claim 1 characterised in that the photo-catalyst diagnoses the biofilm by preferentially staining and disclosing it to a naked eye.

4. The composition as claimed in claim 1 characterised in that the photo-catalyst diagnoses the biofilm by preferentially staining the biofilm and disclosing it when it is illuminated with light including wavelengths which cause it to fluoresce.

5. The composition as claimed in claim 1 characterised in that the photo-catalyst generates light-dependent toxicity that kills bacteria and breaks down the biofilm structure.

6. The composition as claimed in claim 1 characterised in that the photo-catalyst absorbs light of wavelengths from 400 to 700 nm.

7. The composition as claimed in claim 1 characterised in that the composition further comprises one or more photo-catalysts selected from the group consisting of azo dyes, chlorins, chlorophylls, coumarins, metallophthalocyanines, metalloporphyrins, naphthalocyanines, perylenequinones, phenazines, phenothiaziniurns, phenoxaziniums, pheophorbides, pheophytins, porphycenes, porphyrins, purpurins, tetrapyrroles, thiophenes, triarylmethanes and xanthenes.

8. The composition as claimed in claim 1 characterised in that the composition is a gel or solution and further comprises a viscosifier.

9. The composition as claimed in claim 1 characterised in that the composition further comprises one or more of a viscosifier, a humectant, a biofilm-disrupting agent or a surface-active agent.

10. A kit of parts for use in diagnosis and/or treatment of biofilm in wounds comprising: a composition comprising 0.05% to 1.0% by weight of a cationic quaternary ammonium surfactant, 0.1% to 3.0% by weight of a metal chelating agent, and a photo-catalyst which preferentially stains biofilms, wherein the photo-catalyst comprises Rose Bengal, wherein the amount of Rose Bengal present in the composition is from 0.0025% to 0.025% by weight and a light source capable of activating the photo-catalyst to fluoresce so that the biofilm is disclosed and capable of generating light-dependent toxicity such that the composition kills bacteria and breaks down biofilm structure.

11. The kit as claimed in claim 10, characterised in that the light source can operate in two modes, a first mode in which the light source produces light wavelengths in the region 300 nm to 10 nm below the $Abs_{max}$ of the photo-catalyst to enable the biofilm to be diagnosed, and a second mode in which the light source produces light wavelengths in the region of a band 75 nm below the $Abs_{max}$ of the photo-catalyst to enable the biofilm to be treated.

12. The kit as claimed in claim 10 further comprising a wound irrigation solution.

13. The kit as claimed in claim 10 characterised in that it further comprises diaimostic spectacles for use in diagnosing the biofilm wherein the spectacles act to exclude all wavelengths of light below the $Abs_{max}$ of the photo-catalyst.

14. The kit as claimed in claim 10 characterised in that the composition comprises a first photo-catalyst used to diagnose the biolitin and second photo-catalyst used to treat the biofilm.

15. A method of diagnosing a presence of biofilm in a wound comprising the steps of:
  (a) applying to a wound a composition comprising 0.05% to 1.0% by weight of a cationic quaternary ammonium surfactant, 0.1% to 3.0% by weight of a metal chelating agent, and a photo-catalyst which preferentially stains biofilms, wherein the photo-catalyst comprises Rose Bengal, wherein the amount of Rose Bengal present in the composition is from 0.0025% to 0.025% by weight; and
  (b) inspecting the wound for a presence of stained biofilm with a naked eye or with a light source that causes the stained biofilm to fluoresce.

16. The method as claimed in claim 15 characterised in that the fluorescence of the stained biofilm is detected with diagnostic spectacles.

17. A method of treating a wound comprising steps of:
  (a) applying to a wound a composition comprising 0.05% to 1.0% by weight of a cationic quaternary ammonium surfactant, 0.1% to 3.0% by weight of a metal chelating agent, and a photo-catalyst which preferentially stains biofihns, wherein the photo-catalyst comprises Rose Bengal, wherein the amount of Rose Bengal present in the composition is from 0.0025% to 0.0025% by weight;
  (b) inspecting the wound for a presence of stained biofilm with a naked eye or with a light source that causes the stained biofilm to fluoresce; and
  (c) illuminating the wound with a light source that causes the photo-catalyst to generate light-dependent toxicity that kills biofilm bacteria and breaks down biofilm structure.

* * * * *